US008360066B2

(12) United States Patent
Piontek

(10) Patent No.: US 8,360,066 B2
(45) Date of Patent: Jan. 29, 2013

(54) HEADREST FOR A PATIENT-BEARING SURFACE

(75) Inventor: Manfred Piontek, Karlsruhe (DE)

(73) Assignee: Maquet GmbH & Co., KG., Rastatt (DE)

( * ) Notice: Subject to any disclaimer, the term of this patent is extended or adjusted under 35 U.S.C. 154(b) by 1517 days.

(21) Appl. No.: 10/534,837

(22) PCT Filed: Sep. 26, 2003

(86) PCT No.: PCT/EP03/10719

§ 371 (c)(1), (2), (4) Date: Jul. 22, 2005

(87) PCT Pub. No.: WO2004/045481

PCT Pub. Date: Jun. 3, 2004

(65) Prior Publication Data

US 2006/0053556 A1 Mar. 16, 2006

(30) Foreign Application Priority Data

Nov. 18, 2002 (DE) .............................. 202 17 825 U

(51) Int. Cl.
*A61F 11/00* (2006.01)
*A42B 1/06* (2006.01)

(52) U.S. Cl. ........................................... 128/857; 2/410

(58) Field of Classification Search .................. 128/857, 128/845, 846, 869, 871; 2/9, 410, 6.3, 425, 2/6.1, 6.6; 5/622, 643, 637–640; 119/722, 119/837

See application file for complete search history.

(56) References Cited

U.S. PATENT DOCUMENTS

| | | | | |
|---|---|---|---|---|
| 4,279,038 | A * | 7/1981 | Bruckner et al. | 2/425 |
| 6,042,184 | A | 3/2000 | Kofoed | 297/391 |
| 6,112,333 | A * | 9/2000 | Mazzei | 2/410 |
| 6,276,012 | B2 | 8/2001 | Borders | 5/622 |
| 6,374,441 | B1 | 4/2002 | Begell | 5/638 |
| 6,460,207 | B1 * | 10/2002 | Papay et al. | 5/640 |
| 6,490,737 | B1 * | 12/2002 | Mazzei et al. | 2/410 |

FOREIGN PATENT DOCUMENTS

WO WO 01/76403 A1 10/2001

* cited by examiner

*Primary Examiner* — Loan Thanh
*Assistant Examiner* — Tarla Patel
(74) *Attorney, Agent, or Firm* — McCormick, Paulding & Huber LLP

(57) ABSTRACT

A headrest for a patient-bearing surface, having an approximately horseshoe-shaped form and comprising a central section (14) for supporting the back of the head or the forehead, the bearing surface thereof being at least approximately spherical shell-shaped, also comprising two side sections (16) which are arranged at a distance from each other and whose bearing surfaces conform at least approximately to a common cylindrical surface whose axis is parallel to a symmetrical line (20) of the headrest extending between the side surfaces (16). A cheekbone support (18), which protrudes in the direction of the other side section (16), is provided on each side section (16).

8 Claims, 2 Drawing Sheets

IV IV 14 10 40 40 22 20 26 26 18 18 16 16 40 40 24

30 28 12 26 48 38 36 40 38 36 44 42

HEADREST FOR A PATIENT-BEARING SURFACE

CROSS REFERENCE TO RELATED APPLICATIONS

Applicants hereby claim foreign priority benefits under 35 U.S.C. 119 of PCT Patent Application No. PCT/EP2003/010719 filed Sep. 26, 2003 and German Patent Application No. 202 17 825.0 filed Nov. 18, 2002, the disclosures of which are herein incorporated by reference.

BACKGROUND OF THE INVENTION

1. Technical Field

The invention concerns a headrest for a patient-bearing surface, especially that of an operating table.

2. Background Art

A headrest is known from U.S. Pat. No. 6,276,012 B2, which rest consists of a U-shaped part and a plate-shaped section lying between the legs of the U. In the case of a patient lying on his or her back the head of the patient is supported by both of the parts. In the case of the patient lying on his or her stomach the plate-shaped part is swung away so that the head of the patient lies with the forehead on the middle bar of the U, and at least the mouth and nose of the patient lie free. The headrest in its entirety is essentially flat and is cushioned. In the case of the patient lying on his or her back as well as the case of the patient lying on his or her stomach the head is not laterally supported.

From U.S. Pat. No. 6,042,184 a lounge chair is known which is provided with a plate-shaped headrest. In the plate-shaped headrest an opening is formed which is surrounded by a circular, not entirely closed, cushion which is fastened to the plate by push buttons. In this case also, the head of the person can be supported with the person lying on his or her back or with the person lying on his or her stomach, with the face lying free. The headrest is however not well adopted to the shape of human heads and is unsuited to support the head of a patient during an operation where the patient has to be held motionless for a long time and in such a way that the patient is not injured for example by pressure points or the like.

WO 01/76403 A1 shows a headrest including a helmet-like curved rest shell with openings for the eye parts, mouth and nose and a foam material cushion with corresponding openings for the support of the face.

U.S. Pat. No. 6,374,441 B1 shows a headrest for supporting the face of a patient with the rest having a board on which a foam material cushion is arranged and into which cushion is cut a contour with a hollow space for the eye parts, mouth and nose.

The invention has as its object the provision of a headrest of the previously mentioned kind which allows the head of the patient to be securely held in a desired position both in the case of the patient lying on his or her back and the case of the patient lying on his or her stomach, and for the patient to be supported with comfort.

SUMMARY OF THE INVENTION

The invention has as its object the provision of a headrest of the previously mentioned kind which allows the head of the patient to be securely held in a desired position both in the case of the patient lying on his or her back and the case of the patient lying on his or her stomach, and for the patient to be supported with comfort.

For solving this object the headrest of the invention has an approximately horseshoe-shape with a central section for supporting the rear of the head or the forehead, the support surface of which central section has an approximately spherical shell shape, and with two side sections spaced from one another, the support surfaces of which side sections approximately conform to a common cylindrical surface whose axis runs parallel to a line of symmetry of the headrest running between the side sections, with a cheekbone support projecting in the direction toward the opposite side section being formed on each of the side sections.

The headrest of the invention is adapted to the particular shape of the human head and supports the head on suitable surfaces of the skull, namely the rear of the head or the forehead as well as the cheekbones. By way of the spherical shell shape and cylindrical curvature respectively of its sections the head is so bedded that it cannot fall to the side. The cheekbone supports on the side sections make possible on one hand a-good support of the face in the case of the patient lying on his or her stomach, with however the eye parts and the mouth and nose remaining free for inhaling and exhaling as well as for the use of an anesthesia mask or other aids. Because of the anatomically correct shape of the headrest of the invention the weight of the head is distributed in large area fashion over the sections of the headrest so that localized pressures are reduced and thereby even in the case of lengthy operations pressure points on the head, especially on the face, can be avoided.

In contrast to customary headrests in the case of which for lateral support of the head the cushion must be made very thick, that is the head sinks relatively far into the cushion, in the case of the solution according to the invention because of the anatomical shape of the headrest the support cushion can be made thinner. The rest shell is advantageously made of plastic which not only simplifies its manufacture, for example by injection molding methods, but also simplifies the cleaning of the rest shell in daily use of it.

Preferably the support cushion on its side facing the rest shell has at least two stick pins designed for insertion into through going bores in the rest shell. This way the support cushion can be quickly and securely connected with the rest shell and can be easily again removed from it. Both these bores and also the stickpins can be cleaned simply and without a problem. To avoid an unwanted loosening of the support cushion from the rest shell it can be advantageous if the stick pins on a cylindrical shaft each have an elastically resilient band whose diameter is slightly larger than the diameter of the bores, so that the stick pins can be pressed into and removed from the bores in the rest shell only with a certain resistance.

The headrest of the invention can be made as one piece or also can be divided into two mirror image similar partial supports along their line of symmetry. The latter embodiment makes possible a definite suiting of the headrest to different sizes of heads.

For the connecting of the headrest to the patient-bearing surface the headrest or each partial rest can in a known way be connected with a fastening block for holding it to a profiled rail, which rail in turn is fastened to the patient-bearing surface or to a holder connected with the patient-bearing surface. To assure that the patient during an operation does not move his or her head, on the outer edge of each side section an eye can be formed for fastening a belt by means of which the patient's head can be fixed to the headrest.

BRIEF DESCRIPTION OF THE DRAWINGS

Further features and advantages of the invention will be apparent from the following description which in combination with the accompanying drawings explain the invention by way of exemplary embodiments. The drawings are.

DETAILED DESCRIPTION OF THE INVENTION

Figure 1:
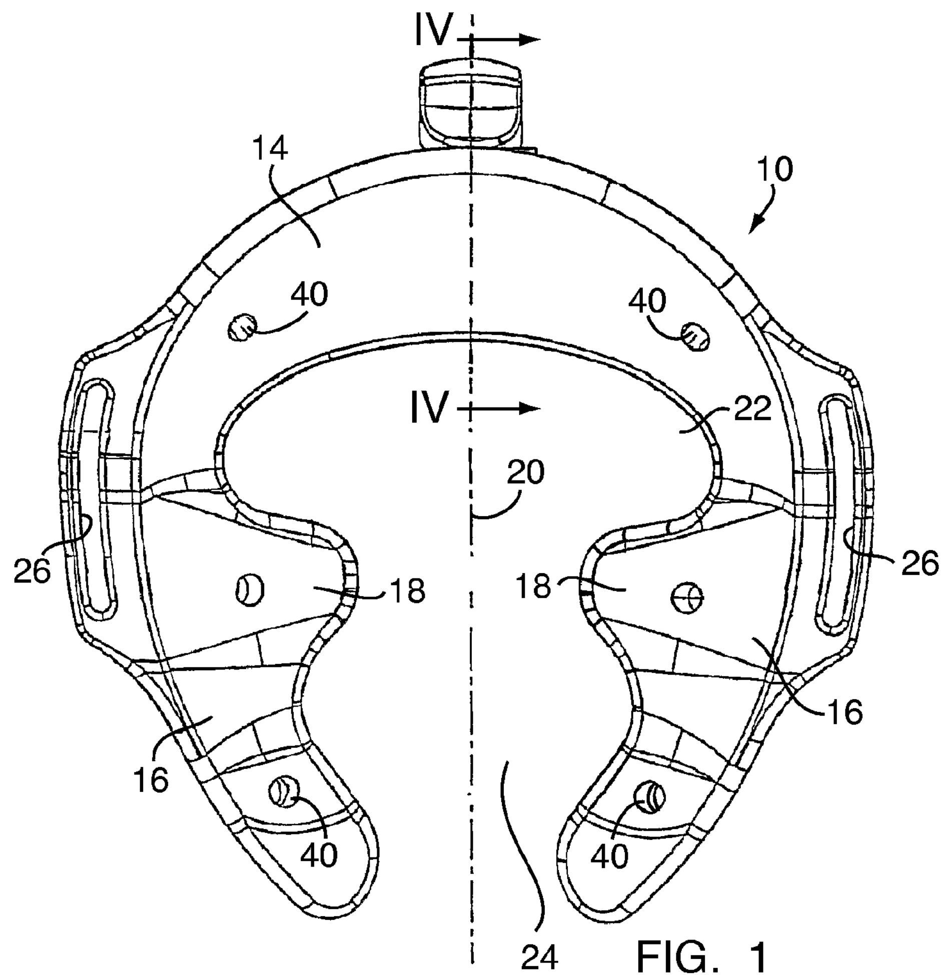
FIG. 1 is a plan view of the support shell of a first embodiment of the headrest of the invention.

The headrest illustrated in FIGS. 1-4 has an approximately horseshoe-shaped form and includes a rest shell, indicated generally at 10, and a support cushion 12 conforming in its shape to that of the shell. The rest shell has a central section 14 designed to support the rear head of a patient (lying on his or her back) or the forehead of a patient (lying on his or her stomach). This central section 14 on its upper or inner side facing the viewer in FIG. 1 is of at least nearly spherical shell shape. Connected to the central section 14 are two side sections 16 which approach one another with their free ends and each of which has a section 18 protruding toward the other side section 16, which sections 18 form a cheekbone support, that is a support which supports in the region of the cheekbones the face of a patient lying on his or her stomach. The side sections 16 conform approximately to a common cylindrical surface whose axis is parallel to the line of symmetry 20 of the headrest and which line of symmetry runs between the two side sections 16. The central opening of the headrest 10 includes a region 22 near the central section 14 which corresponds to the eye parts of the patient's face and a region 24 corresponding to the mouthparts of the patient's face. By the suiting of the rest shell 14 to the anatomical shape of the head on one hand a better lateral support and on the other hand a support of increased surface area of the head on the headrest is achieved, so that in turn localized pressure loading and therewith the risk of forming pressure points on the head of the patient is reduced.

Figure 2:
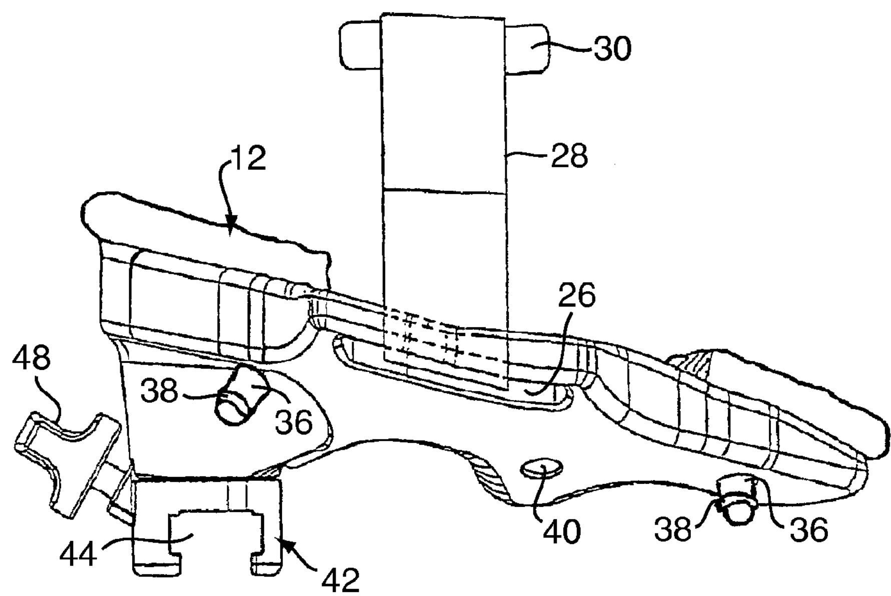
FIG. 2 is a side view of a headrest provided with a support cushion and a fixing belt.

On the outer edge of each side section 16 is an eye 26 through which a belt 28 can be pulled by means of which the head of a patient can be fixed to the head support. The belt 28 in doing this is pulled through the eyes 26, following which the ends of the belt are overlapped with one another and are for example fastened by means of a Velcro fastener, as is indicated in FIG. 2. On the inner side of the belt is a pillow 30 through which the belt lies onto the head of the patient.

Figure 3:
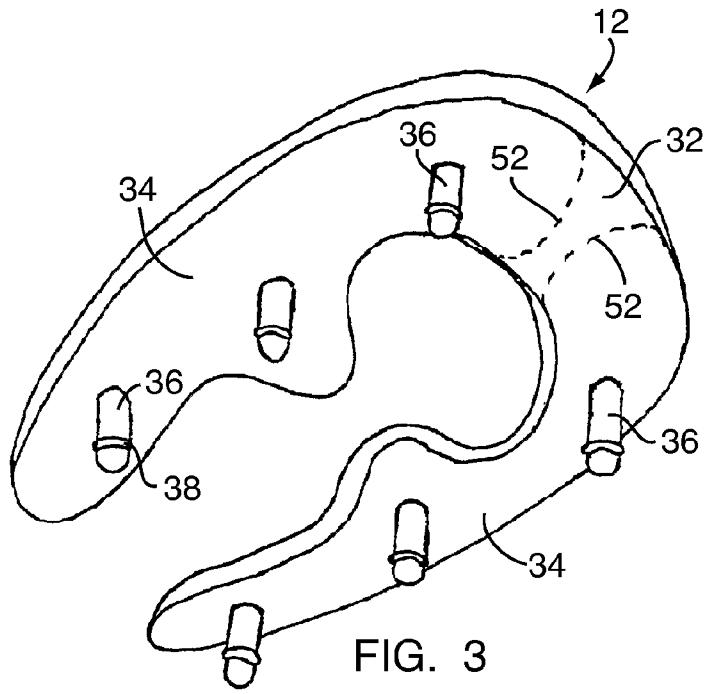
FIG. 3 is a perspective bottom view of a support cushion intended for a support shell according to FIG. 1.

The support cushion which is connected with the rest shell according to FIG. 1 is illustrated in FIG. 3. It has a form which suits the shape of the rest shell 10 with a central section 32 and side sections 34. On its side facing the rest shell 10 the support cushion carries stickpins 36 which are formed essentially cylindrically and each of which in a circumferential groove carries an O-ring 38. The stick pins 36 are insertable into bores 40 formed in the rest shell 10 with the measurements of the bores 40 and of the stick pins 36 being so chosen that upon the insertion and withdrawal of the stick pins 36 into or out of the bores 40 a certain opposing resistance is created. The support cushion 12 can however in this way be quickly connected to or removed from the rest shell 10 so that the rest shell 10 and the support cushion 12 can be easily cleaned hygienically and without problem.

Figure 4:
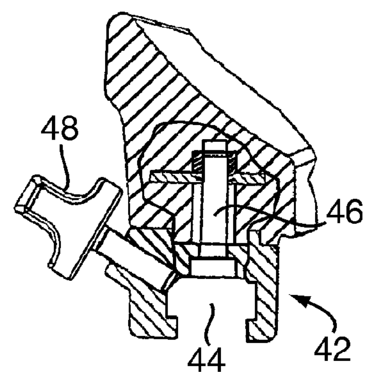
FIG. 4 is a partial section through the support shell taken along the line IV-IV in FIG. 1.

FIG. 4 shows a fastening block 42 connected with the rest shell which block has a profiled opening 44 which is slidable onto a shaped rail and is fixed to the rest shell 10 by a screw 46. By means of a clamping screw 48 the block 42 and thereby the entire headrest can be fixed to the shaped rail.

Figure 5:
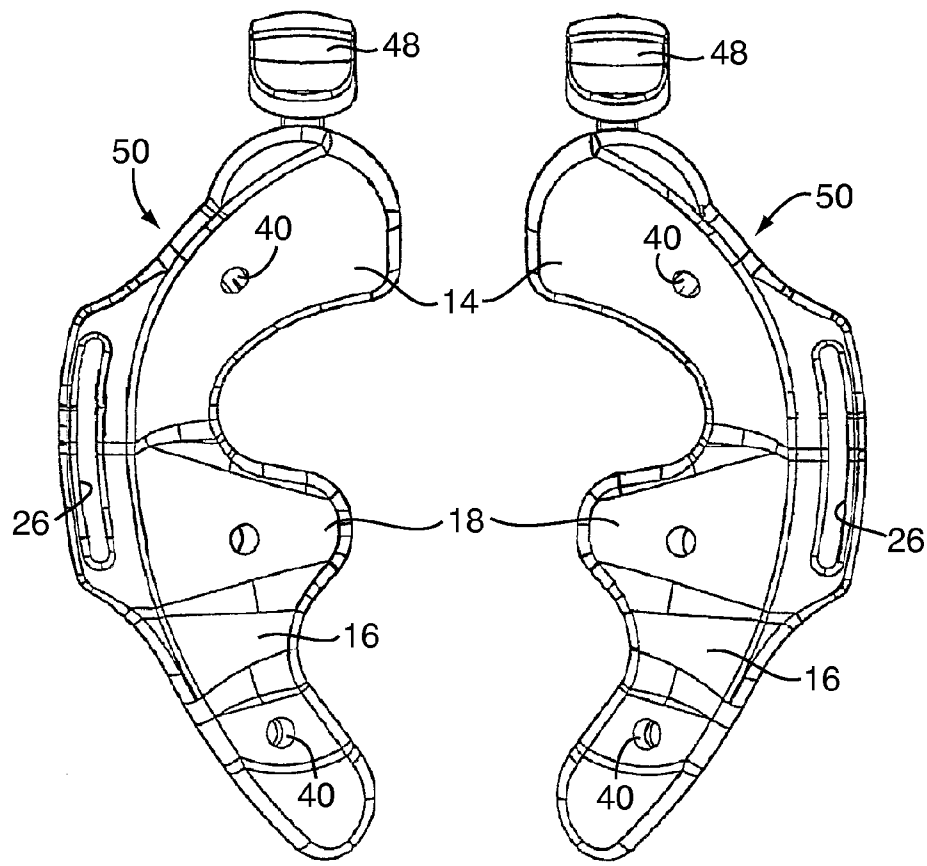
FIG. 5 is a plan view corresponding to FIG. 1 of a rest shell of a headrest according to a second embodiment of the invention.

FIG. 5 shows a two-part rest shell for a two-part headrest. The two partial shells 50 are formed mirror image symmetrical to one another with respect to the line of symmetry 20 and correspond in all details to the corresponding sections of the one piece rest shell of FIG. 1 with the exception that each partial shell 50 is provided with a fastening block 42. The associated support cushion is divided similarly to the rest shell, as this is indicated in FIG. 3 by the broken lines 52. The embodiment according to FIG. 5 offers the possibility of changing the spacing between the two partial rests of the headrest to suit the size of the head to be supported.

While the present invention has been illustrated and described with respect to a particular embodiment thereof, it should be appreciated by those of ordinary skill in the art that various modifications to this invention may be made without departing from the spirit and scope of the present invention.

What is claimed is:

1. A headrest for a patient-bearing surface, comprising:

a rigid support shell, the support shell having an approximately horseshoe-shaped form; and a support cushion releasably connectable with the support shell;

wherein the support shell includes a central section for supporting the rear or forehead of a head of a patient and having a support surface of approximately spherical shell shape, two side sections spaced from one another, the side sections each having a support surface of approximately a common cylindrical shape whose axis runs parallel to a line of symmetry of the support shell, and a cheekbone support on each of the side sections, each cheekbone support projecting toward the other side section.

2. The headrest according to claim 1, wherein the support shell is made of plastic.

3. The headrest according to claim 1, wherein the support cushion on its side facing the support shell carries at least two stick pins designed for insertion into through going bores in the support shell.

4. The headrest according to claim 3, wherein the stick pins each have a cylindrical shaft which the cylindrical shaft having an elastically resilient band with an external diameter slightly larger than a diameter of the bores.

5. The headrest according to claim 1, wherein the support shell is divided into two mirror image similar partial shells along the line of symmetry.

6. The headrest according to claim 1, wherein the support shell or each partial shell is connected to a fastening block for holding the support shell or partial shell to a profiled rail.

7. The headrest according to claim 1, wherein an eye is formed on the outer edge of each side section for fastening a belt to fix the head of the patient to the headrest.

8. A headrest for a patient-bearing surface comprising:

a rigid support shell having an approximately horseshoe-shaped form; and a support cushion releasably connectable with the support shell;

wherein the support shell includes a central section for supporting the rear or forehead of a head of a patient and having a support surface of approximately spherical shell shape, two side sections spaced from one another, the side sections each having a support surface of approximately a common cylindrical shape whose axis runs parallel to a line of symmetry of the support shell, and a cheekbone support on each of the side sections, each cheekbone support projecting toward the other side section; and wherein the side sections include end portions separated from each other to define an open region for mouthparts of the patient's face to fit therein.

* * * * *